US009475756B2

(12) United States Patent
Hartwig et al.

(10) Patent No.: US 9,475,756 B2
(45) Date of Patent: Oct. 25, 2016

(54) DIFLUOROMETHYLATION OF ARYL AND VINYL IODIDES

(71) Applicant: THE REGENTS OF THE UNIVERSITY OF CALIFORNIA, Oakland, CA (US)

(72) Inventors: John Hartwig, Berkeley, CA (US); Patrick Fier, Berkeley, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 14/382,991

(22) PCT Filed: Mar. 5, 2013

(86) PCT No.: PCT/US2013/029172
§ 371 (c)(1),
(2) Date: Sep. 4, 2014

(87) PCT Pub. No.: WO2013/134296
PCT Pub. Date: Sep. 12, 2013

(65) Prior Publication Data
US 2015/0045580 A1    Feb. 12, 2015

Related U.S. Application Data

(60) Provisional application No. 61/606,925, filed on Mar. 5, 2012.

(51) Int. Cl.
| | | |
|---|---|---|
| C07B 39/00 | (2006.01) | |
| C07C 17/263 | (2006.01) | |
| C07C 17/32 | (2006.01) | |
| C07C 209/68 | (2006.01) | |
| C07C 231/12 | (2006.01) | |
| C07C 41/30 | (2006.01) | |
| C07C 41/48 | (2006.01) | |
| C07C 41/56 | (2006.01) | |
| C07C 67/293 | (2006.01) | |

(52) U.S. Cl.
CPC ............ *C07C 231/12* (2013.01); *C07B 39/00* (2013.01); *C07C 17/263* (2013.01); *C07C 17/32* (2013.01); *C07C 41/30* (2013.01); *C07C 41/48* (2013.01); *C07C 41/56* (2013.01); *C07C 67/293* (2013.01); *C07C 209/68* (2013.01); *C07B 2200/09* (2013.01)

(58) Field of Classification Search
CPC . C07B 39/00; C07B 2200/09; C07C 17/263; C07C 17/32; C07C 209/68; C07C 231/12; C07C 41/30; C07C 41/48; C07C 41/56; C07C 67/293
See application file for complete search history.

(56) References Cited

U.S. PATENT DOCUMENTS

2005/0215794 A1    9/2005  Buchwald et al.

OTHER PUBLICATIONS

Fier et al.,"Copper-Mediated Difluoromethylation of Aryl and Vinyl Iodides," J. Am. Chem. Soc., 2012, 134, 5524-5527.*
Burton and Hartgraves, "The preparation of $HCF_2CdX$ and $HCF_2ZnX$ via direct insertion into the carbon halogen bond of $CF_2HY$ (Y = BR, I)." Journal of Fluorine Chemistry, vol. 128, pp. 1198-1215 (2007).
Erickson and McLoughlin, "Hydrogen Bond Donor Properties of the Difluoromethyl Group." J. Org. Chem., vol. 60, pp. 1626-1631 (1995).
Eujen, R. et al., "Synthesis and properties of donor-free bis(difluoromethyl) cadmium, $(CF_2H)_2Cd$ NMR spectroscopic detection and structure of tetrakis(difluoromethyl) cuprate(III) and related compounds." Journal of Organometallic Chemistry, vol. 519, pp. 7-20 (1996).
Fujiwara, Y. et al., "A New Reagent for Direct Difluoromethylation." J. Am. Chem. Soc., vol. 134, No. 3, pp. 1494-1497 (2012).
Fujikawa, K. et al., "A New Method for Aromatic Difluoromethylation: Copper-Catalyzed Cross-Coupling and Decarboxylation Sequence from Aryl Iodides." Organic Letters, vol. 13, No. 20, pp. 5560-5563 (2011).
Furuya, T. et al., "Catalysis for fluorination and trifluoromethylation." Nature, vol. 473, pp. 470-477 (2011).
Hu, J. et al., "Selective difluoromethylation and monofluoromethylation reactions." Chem. Commun., pp. 7465-7478 (2009).
Markovski, L. et al., "Application of Dialkylaminosulfur Trifluorides in the Synthesis of Fluoroorganic Compounds.", Synthesis, pp. 787-789 (1973).
Meanwell, N., "Synopsis of Some Recent Tactical Application of Bioisosteres in Drug Design." Journal of Medicinal Chemistry, vol. 54, pp. 2529-2591 (2011).

(Continued)

*Primary Examiner* — Paul A Zucker
*Assistant Examiner* — Mark Luderer
(74) *Attorney, Agent, or Firm* — Morgan, Lewis & Bockius LLP; Jeffry S. Mann

(57) ABSTRACT

Selectively fluorinated molecules are important as materials, pharmaceuticals, and agrochemicals, but their synthesis by simple, mild, laboratory methods is challenging. We report a straightforward method for the cross-coupling of a difluoromethyl group with readily available reagents to form difluoromethylarenes. The reaction of electron-neutral, electron rich, and sterically hindered aryl and vinyl iodides with the combination of CuI, CsF and $TMSCF_2H$ leads to the formation of difluoromethylarenes in high yield with good functional group compatibility. This transformation is surprising, in part, because of the prior observation of the instability of $CuCF_2H$.

25 Claims, No Drawings

(56) References Cited

OTHER PUBLICATIONS

Middleton, W., "New Fluorinating Reagents. Dialkylaminosulfur Fluorides." J. Org. Chem., vol. 40, No. 5, pp. 574-578 (1975).

Sheppard, T., "Metal-catalysed halogen exchange reactions of aryl halides." Org. Biomo. Chem., vol. 7, pp. 1043-1052 (2009).

Tomashenko and Grushin, "Aromatic Trifluoromenthylation with Metal Complexes.", Chemical Reviews, pp. 4475-4521 (2011).

\* cited by examiner

DIFLUOROMETHYLATION OF ARYL AND VINYL IODIDES

CROSS-REFERENCE TO RELATED APPLICATIONS

This application claims under 35 USC 119(e) the benefit of U.S. Provisional Application No. 61/606,925, filed Mar. 5, 2012, which is incorporated herein by reference in its entirety for all purposes.

STATEMENT AS TO RIGHTS TO INVENTIONS MADE UNDER FEDERALLY SPONSORED RESEARCH OR DEVELOPMENT

This invention was made with Government support under Grant No. GM-58108 awarded by the NIH-NIGMS. The Government has certain rights in this invention.

BACKGROUND OF THE INVENTION

The unique stability, reactivity and biological properties of fluorinated compounds contribute to their widespread use in many chemical disciplines. Compounds containing a trifluoromethyl group have been studied extensively. Compounds containing partially fluorinated alkyl groups, such as a difluoromethyl group, should be similarly valuable for medicinal chemistry because such groups could act as lipophilic hydrogen bond donors and as bio-isosteres of alcohols and thiols (Erickson, J. A.; McLoughlin, J. I. *J. Org. Chem.* 1995, 60, 1626, Meanwell, N. A. *J. Med. Chem.* 2011, 54, 2529). However, methods for the introduction of a difluoromethyl group are limited, and methods for the introduction of a difluoromethyl group onto arenes are even more limited. Hence there is a current need for new procedures to generate difluoromethylarenes (Hu, J.; Zhang, W.; Wang, F. *Chem. Commun.* 2009, 7465).

Most current syntheses of difluoromethylarenes require hazardous reagents or multi-step sequences (Scheme 1). Fluoro-deoxygenation of aldehydes with sulfur tetrafluoride or aminosulfurtrifluorides (DAST, Deoxofluor) is the most common route to difluoromethyl compounds. However, these reagents release hydrogen fluoride upon contact with water and may undergo explosive decomposition when heated (Markovski, L. N.; Pahinnik, V. E.; Kirsanov, A. V. *Synthesis* 1973, 787, Middleton, W. J. *J. Org. Chem.* 1975, 40, 574). Amii and coworkers recently reported a three-step route to difluoromethylarenes; however, the final step of this process only occurred with electron-deficient aryl iodides, and the three-step process with electron-poor arenes occurred in modest overall yields (Scheme 1) (Fujikawa, K.; Fujioka, Y.; Kobayashi, A.; Amii, H. *Org. Lett.* 2011, 13, 5560). Baran recently reported a new reagent that leads to the addition of difluoromethyl radicals to heteroaromatic systems under mild conditions (Fujiwara, Y.; Dixon, J. A.; Rodriguez, R. A.; Baxter, R. D.; Dixon, D. D.; Collins, M. R.; Blackmond, D. G.; Baran, P. S. *J. Am. Chem. Soc.* 2012, 134, 1494). However, reactions with arenes were not reported. Thus, methods for the introduction of a difluoromethyl group onto arenes and methods for the introduction of the difluoromethyl group with regioselectivities that complement those resulting from radical-based reactions are needed.

Scheme. Preparation of Difluoromethylarenes

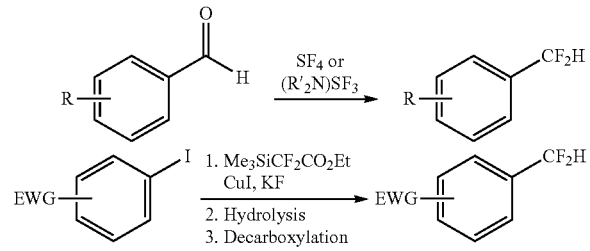

SUMMARY OF THE INVENTION

The present invention provides methods and compositions for the difluoromethylation of aryl and vinyl compounds. In an exemplary method, the difluoromethylation is accomplished in a single step. The methods and compositions of the invention are highly versatile and are compatible with a wide range of substrates having a great variety of functional groups.

In contrast to the recent success in developing copper-mediated trifluoromethylation of aryl halides (Tomashenko, O. A.; Grushin, V. V. *Chem. Rev.* 2011, 111, 4475), methods for related copper-mediated difluoromethylation of aryl halides have not been developed. Difluoromethyl copper complexes are much less stable than trifluoromethyl copper complexes and are known to be unstable toward the formation of tetrafluoroethane and cis-difluoroethylene (Hu, J.; Zhang, W.; Wang, F. *Chem. Commun.* 2009, 7465, Eujen, R.; Hoge, B.; Brauer, D. J. *J. Organomet. Chem.* 1996, 519, 7, Burton, D. J.; Hartgraves, G. A. *J. Fluorine Chem.* 2007, 128, 1198). Despite this instability, the present invention provides compositions and methods for copper-mediated difluoromethylation of aryl and vinyl iodides.

In an exemplary embodiment, the present invention provides a reaction mixture for forming a difluoromethyl aryl compound or a difluoromethyl vinyl compound. The reaction mixture comprises: (i) a member selected from an X-substituted precursor of the difluoromethyl aryl compound and an X-substituted precursor of the difluoromethyl vinyl compound, wherein X is a leaving group (e.g., iodo or bromo); (ii) a Cu source; (iii) a fluoride ion source; and (iv) a silane having the formula:

$R^1R^2R^3SiCF_2H$ wherein $R^1$, $R^2$ and $R^3$ are independently selected from substituted or unsubstituted alkyl, substituted or unsubstituted alkoxy and substituted or unsubstituted aryl moieties. In various embodiments, the precursor is optionally further substituted at one or more positions with an "aryl group substituent" or an "alkyl group" substituent such as those set forth herein.

Also provided are methods of preparing difluoromethyl-aryl and -vinyl compounds using a reaction mixture of the invention.

Additional objects, advantages and embodiments of the invention are set forth in the detailed description below.

DETAILED DESCRIPTION OF THE EMBODIMENTS

I. Introduction

The ability to selectively difluoromethylate an aryl or vinyl substrate has broad application, especially in the agricultural, pharmaceutical, and polymer industries. As described herein, the present invention relates to compositions and methods for transforming an aryl or vinyl substrate to the corresponding difluoromethyl compound. The compositions and methods of the invention utilize simple, readily available substrates and reaction mixture and, thus, have wide applicability.

In various embodiments, the present invention provides a one-step procedure for the difluoromethylation of aryl and vinyl substrates that occurs with readily available and non-hazardous reagents. This reaction tolerates a wide range of substituents, e.g., amine, ether, amide, ester, aromatic bromide and protected alcohol functionalities, and occurs in high yield even with sterically hindered substrates. The simplicity and generality of this method makes it attractive for the introduction of a $CF_2H$ group into functionally diverse arenes and vinyl compounds.

In various embodiments, the invention is directed to the aforementioned need in the art, and provides a new technique and compositions for effecting difluoromethylation of an aryl or vinyl precursor. The method involves contacting the precursor with a copper source (e.g., Cu(0), Cu(I) or Cu(II); a fluoride ion source; and a silane having the formula:

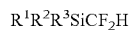

$$R^1R^2R^3SiCF_2H$$

wherein $R^1$, $R^2$ and $R^3$ are independently selected from substituted or unsubstituted alkyl, substituted or unsubstituted alkoxy and substituted or unsubstituted aryl moieties.

Accordingly, the invention also provides a reaction mixture containing components of use to practice the method set forth above.

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

In describing the present invention, the following terms will be employed, and are intended to be defined as indicated below.

Definitions

Where substituent groups are specified by their conventional chemical formulae, written from left to right, the structures optionally also encompass the chemically identical substituents, which would result from writing the structure from right to left, e.g., —$CH_2O$— is intended to also optionally recite —$OCH_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di-, tri- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to optionally include those derivatives of alkyl defined in more detail below, such as "heteroalkyl." Alkyl groups that are limited to hydrocarbon groups are termed "homoalkyl". Exemplary alkyl groups include the monounsaturated $C_{9-10}$, oleoyl chain or the diunsaturated $C_{9-10, 12-13}$ linoeyl chain.

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The terms "aryloxy" and "heteroaryloxy" are used in their conventional sense, and refer to those aryl or heteroaryl groups attached to the remainder of the molecule via an oxygen atom.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$CO_2$R'— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Further exemplary cycloalkyl groups include steroids, e.g., cholesterol and its derivatives. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxyl)propyl, and the like).

Each of the above terms (e.g., "alkyl," "heteroalkyl," "aryl" and "heteroaryl") are meant to optionally include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: H, substituted or unsubstituted aryl, substituted or unsubstituted heteroaryl, substituted or unsubstituted heterocycloalkyl, —OR', =O, =NR', =N—OR', —NR'R", —SR', halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR", —NR—C(NR'R")=NR'", —S(O)R', —S(O)$_2$R', —S(O)$_2$NR'R", —NRSO$_2$R', —CN and —$NO_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R"

is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —$C(O)CH_3$, —$C(O)CF_3$, —$C(O)CH_2OCH_3$, and the like). These terms encompass groups considered exemplary "alkyl group substituents", which are components of exemplary "substituted alkyl" and "substituted heteroalkyl" moieties.

Similar to the substituents described for the alkyl radical, substituents for the aryl and heteroaryl groups are generically referred to as "aryl group substituents." The substituents are selected from, for example: H, substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R''', —OC(O)R', —C(O)R', —$CO_2$R', —CONR'R", —OC(O)NR'R", —NR"C(O)R', —NR'—C(O)NR"R''', —NR"C(O)$_2$R', —NR—C(NR'R"R''')=NR", —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R''' and R'''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R''' and R'''' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_q$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted ($C_1$-$C_6$)alkyl. These terms encompass groups considered exemplary "aryl group substituents", which are components of exemplary "substituted aryl" and "substituted heteroaryl" moieties.

As used herein, the term "acyl" describes a substituent containing a carbonyl residue, C(O)R. Exemplary species for R include H, halogen, substituted or unsubstituted alkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems may include aromatic as well as non-aromatic rings. Examples of "fused ring systems" are naphthalenes, indoles, quinolines, chromenes and the like.

As used herein, the term "heteroatom" includes oxygen (O), nitrogen (N), sulfur (S) and silicon (Si) and boron (B).

The symbol "R" is a general abbreviation that represents a substituent group that is selected from H, substituted or unsubstituted alkyl, substituted or unsubstituted heteroalkyl, substituted or unsubstituted aryl, substituted or unsubstituted heteroaryl, and substituted or unsubstituted heterocycloalkyl groups.

The terms "substrate" and "precursor" are used interchangeably and refer to compound with a leaving group substitutable by a difluoromethyl synthon in a method and composition of the invention. An exemplary substrate or precursor is an iodo-substituted aryl or vinyl compound which can react under the conditions of the invention, to yield at least one product having a difluoromethyl moiety.

The compounds disclosed herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

As used herein, "electron neutral", "electron donating" and "electron withdrawing" refer to the net electronic effect of substituents on an aryl nucleus. The concept underlying electron neutral, electron donating and electron withdrawing substituents (e.g., aryl group substituents) is well-understood in the art and has been so for many years. Frameworks such as the Crum Brown-Gibson Rule (*J. Chem Soc.* 61, 367 (1892)) and the Hammett Equation (Hammett, Louis P. *J. Am. Chem. Soc.* 59, 96 (1937)) are a useful guide for the selection of individual substituents and combinations of substituents having electron neutral or electron donating properties. The selection of substituted aryl groups functioning within the methods of the invention utilizing the Crum Brown-Gibson Rule and Hammett Rule is a component of the instant invention.

The term "ligand" has the meaning ordinarily ascribed to it in the art. Exemplary ligands include at least one donor atom capable of binding to Cu(0), Cu(I) or Cu(II). Ligands can include sterically bulky species, such as substituted or unsubstituted aryl, substituted or unsubstituted heteroaryl and substituted or unsubstituted fused ring systems, secondary and tertiary alkyl groups and the like. An exemplary ligand is substituted or unsubstituted phenanthroline.

The term "salt(s)" includes salts of the compounds prepared by the neutralization of acids or bases, depending on the particular ligands or substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium salt, or a similar salt. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Certain specific compounds of the present invention contain both basic and acidic functionalities that allow the compounds to be converted into either base or acid addition salts. Hydrates of the salts are also included.

The compounds disclosed herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Below are examples of specific embodiments for carrying out the present invention. The examples are offered for illustrative purposes only, and are not intended to limit the scope of the present invention in any way.

The Compositions

In an exemplary embodiment, the present invention provides a reaction mixture for forming a difluoromethyl aryl compound or a difluoromethyl vinyl compound. The reaction mixture comprises: (i) a member selected from a leaving group-substituted precursor of the difluoromethyl aryl compound and an leaving group-substituted precursor of the difluoromethyl vinyl compound; (ii) a Cu source; (iii) a fluoride ion source; and (iv) a silane having the formula:

$$R^1R^2R^3SiCF_2H$$

wherein $R^1$, $R^2$ and $R^3$ are independently selected from substituted or unsubstituted alkyl, substituted or unsubstituted alkoxy and substituted or unsubstituted aryl moieties. In various embodiments, the precursor is optionally further substituted at one or more positions with an "aryl group substituent" or an "alkyl group" substituent such as those set forth herein.

Useful leaving groups are conveniently selected from any such group that can be substituted by a difluoromethyl synthon using a reaction mixture of the invention in a method of the invention. In various embodiments, the leaving groups are selected from iodide, bromide, mesylate, tresylate and triflate. Other appropriate leaving groups will be apparent to those of skill in the art. In an exemplary embodiment, the leaving group is iodide.

The reaction mixture functions to transform aryl and vinyl substrates of a broad range of structures to difluoromethyl compounds. For example, in addition to the leaving group, the precursor is optionally further substituted with an amine, ether, amide, ester, bromide, protected alcohol or a combination thereof.

In an exemplary embodiment, the substrate is an aryl compound having a structure which is a member selected from:

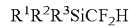

wherein $R^4$, $R^5$, $R^6$, $R^7$, and $R^8$ are independently members selected from H, substituted or unsubstituted alkyl, substituted or unsubstituted heteroalkyl, substituted or unsubstituted aryl, substituted or unsubstituted heteroaryl, halogen, CN, CF$_3$, acyl, —SO$_2$NR$^9$R$^{10}$, —NR$^9$R$^{10}$, —OR$^9$, —S(O)$_2$R$^9$, —C(O)R$^9$, —COOR$^9$, —CONR$^9$R$^{10}$, —S(O)$_2$OR$^9$, —OC(O)R$^9$, —C(O)NR$^9$R$^{10}$, —NR$^9$C(O)R$^{10}$, —NR$^9$SO$_2$R$^{10}$ and —NO$_2$, wherein two or more of $R^4$, $R^5$, $R^6$, $R^7$ and $R^8$, together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl. X is a leaving group, e.g., iodo or bromo.

The symbols $R^9$ and $R^{10}$ represent members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and $R^9$ and $R^{10}$, together with the atoms to which they are bonded, are optionally joined to form a 5- to 7-membered ring which is a member selected from substituted or unsubstituted cycloalkyl, substituted or unsubstituted heterocycloalkyl, substituted or unsubstituted aryl and substituted or unsubstituted heteroaryl.

The moieties $R^4$, $R^5$, $R^6$, $R^7$, and $R^8$ are selected such that the net electronic effect of these moieties on the aryl moiety of said precursor is electron neutral, electron withdrawing or electron donating. In an exemplary embodiment, the effect is electron neutral or electron donating.

An example of the diversity of aryl substrates of use in the reaction mixtures and methods of the invention is set forth in Table 1:

TABLE 1

Difluoromethylation of Aryl Iodides with TMSCF$_2$H Mediated by Copper Iodide$^a$

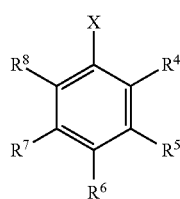

TABLE 1-continued

Difluoromethylation of Aryl Iodides with TMSCF₂H Mediated by Copper Iodide[a]

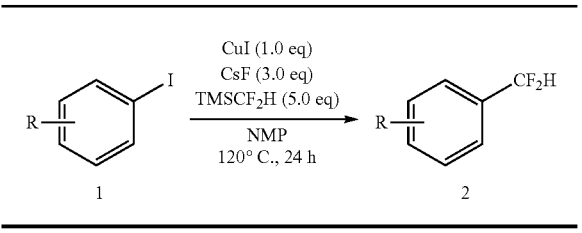

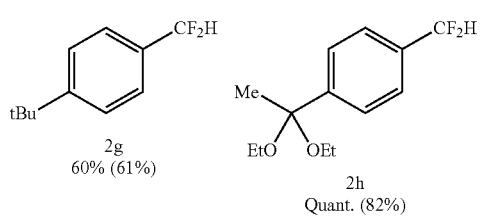 [SMILES: CC(C)(C)c1ccc(C(F)F)cc1 ; CCOC(C)(OCC)c1ccc(C(F)F)cc1]

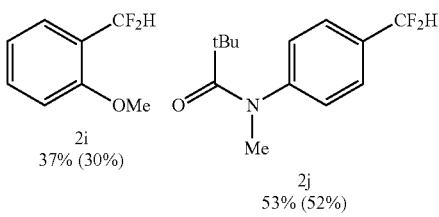

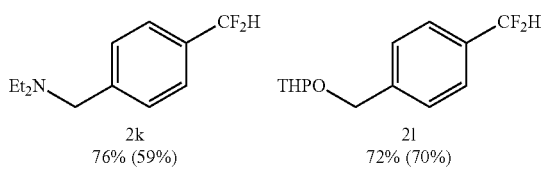

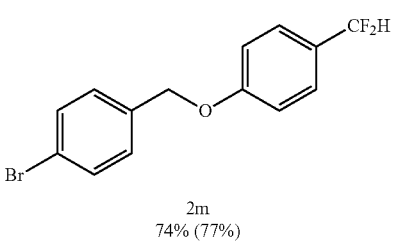 [SMILES: FC(F)c1ccc(OCc2ccc(Br)cc2)cc1]

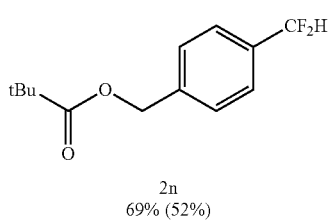 [SMILES: CC(C)(C)C(=O)OCc1ccc(C(F)F)cc1]

[a]Reactions were performed with 0.1 mmol of aryl iodide to determine ¹⁹F NMR yields with 1-bromo-4-fluorobenzene as an internal standard. Isolated yields, shown in parenthesis, were obtained from reactions performed with 0.5 mmol of aryl iodide.

In various embodiments, the invention provides a reaction mixture for transforming a leaving group-vinyl substrate to the corresponding difluoromethyl vinyl analogue. In these embodiments, the leaving group is as set forth above.

In an exemplary embodiment, the leaving group-vinyl precursor has the formula:

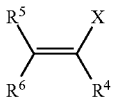

wherein $R^4$, $R^5$, and $R^6$ are independently members selected from H, substituted or unsubstituted alkyl, substituted or unsubstituted heteroalkyl, substituted or unsubstituted aryl, substituted or unsubstituted heteroaryl, halogen, CN, $CF_3$, acyl, $-SO_2NR^9R^{10}$, $-NR^9R^{10}$, $-OR^9$, $-S(O)_2R^9$, $-C(O)R^9$, $-COOR^9$, $-CONR^9R^{10}$, $-S(O)_2OR^9$, $-OC(O)R^9$, $-C(O)NR^9R^{10}$, $-NR^9C(O)R^{10}$, $-NR^9SO_2R^{10}$ and $-NO_2$. Two or more of $R^4$, $R^5$, $R^6$, $R^7$ and $R^8$, together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl. $R^9$ and $R^{10}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and $R^9$ and $R^{10}$, together with the atoms to which they are bonded, are optionally joined to form a 5- to 7-membered ring. X is a leaving group, e.g., iodo or bromo.

An example of the diversity of vinyl substrates of use in the reaction mixtures and methods of the invention is set forth in Table 2:

TABLE 2

Difluoromethylation of Vinyl Iodides with TMSCF2H Mediated by Copper Iodide[a]

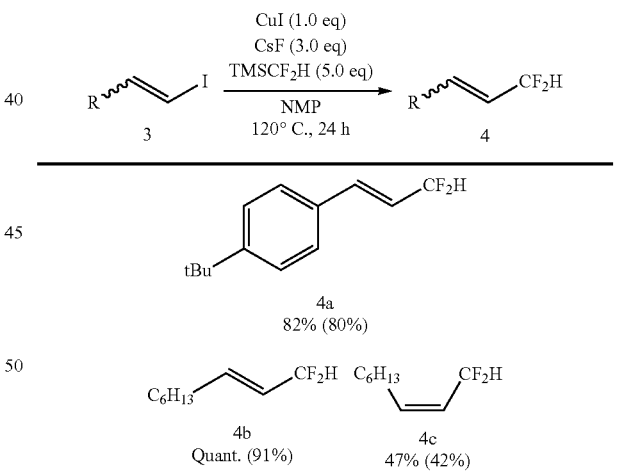

[a]Reactions were performed with 0.1 mmol of vinyl iodide to determine ¹⁹F NMR yields with 1-bromo-4-fluorobenzene as an internal standard. Isolated yields, shown in parenthesis, were obtained from reactions with 0.5 mmol of vinyl iodide.

As will be appreciated by those of skill in the art, though they generically represent iodo compounds, the formulae set forth above are equally applicable to precursors substituted with a leaving group which is not an iodo moiety (e.g., Br, Ms, Ts, Tf).

The reaction mixture can further include a solvent and this solvent can be any compound or mixture of compounds useful to dissolve at least a portion of one or more component of the reaction mixture. In an exemplary embodiment, the solvent is a polar organic solvent, e.g., N-methylpyrrolidone.

The copper source in the reaction mixture can be of any useful formula and form, however, in exemplary embodiments, the copper source is selected from a copper salt and a copper complex with one or more ligand. The copper can be Cu(0), Cu(I) or Cu(II). In an exemplary embodiment, the copper source is CuI.

Silanes of various substitution patterns are of use in the reaction mixture and methods of the invention. In an exemplary embodiment, the silane is selected for the simplicity of its structure and/or its ready availability. For example, in one embodiment, $R^1$, $R^2$ and $R^3$ are each methyl or ethyl.

The reaction mixture also includes a source of fluoride. The fluoride source can be of any useful formula or form with the proviso that it provides sufficient fluoride ion for the difluoromethylation reaction to occur. In an exemplary embodiment, the fluoride ion source is CsF, KF, NaF, LiF, $R_4N^+R'SiF_2^-$, $R_4P^+F^-$, and the like.

As shown in Table 3, various ratios of precursor to copper source to fluoride source to silane are of use in reaction mixtures of the invention. In an exemplary embodiment, the precursor, the Cu(I) source, CsF and the silane are present in the reaction mixture in a ratio of about 1:1:3:5.

TABLE 3

Effect of Copper Source and Reagent Ratios on the Difluoromethylation of 1-butyl-4-iodobenzene[a]

| Entry | CuX (eq) | CsF (eq) | TMSCF$_2$H (eq) | yield (%) |
|---|---|---|---|---|
| 1 | cuBr (1.0) | 2.0 | 5.0 | 84 |
| 2 | CuBr—SMe$_2$ (1.0) | 2.0 | 5.0 | 70 |
| 3 | CuCl (1.0) | 2.0 | 5.0 | 53 |
| 4 | CuI (1.5) | 1.5 | 1.5 | 26 |
| 5 | CuI (3.0) | 3.0 | 3.0 | 36 |
| 6 | CuI (1.0) | 1.0 | 5.0 | 55 |
| 7 | CuI (1.0) | 2.0 | 5.0 | 91 |
| 8 | CuI (1.0) | 3.0 | 3.0 | 75 |
| 9 | CuI (1.0) | 3.0 | 5.0 | 100 |

[a]Reactions were performed with 0.1 mmol of 1-butyl-4-iodobenzene in 0.5 mL of NMP for 24 hours. The yield was determined by $^{19}$F NMR with 1-bromo-4-fluorobenzene as an internal standard.

The Methods

In various embodiments, the present invention provides methods for converting an aryl or vinyl compound functionalized with a leaving group in to a difluoromethyl-aryl or -vinyl compound. In an exemplary embodiment, the method includes: (a) forming a reaction mixture as set forth herein; and (b) incubating the reaction mixture under conditions appropriate to form the difluoromethyl aryl compound or the difluoromethyl vinyl compound by substituting the leaving group with a CF$_2$H moiety. In an exemplary embodiment, the leaving group is an iodo moiety.

According to the method of the invention, any useful temperature or range of temperatures can be used to convert the precursor to the desired product. In an exemplary embodiment, the reaction mixture is incubated at a temperature from about 50° C. to about 180° C., e.g., about 80° C. to about 140° C., e.g., about 120° C.

The reaction mixture can be incubated for any useful length of time. In various embodiments, the invention is incubated at a desired temperature for about 1 hour to about 36 hours, e.g., for about 6 hours to about 24 hours.

The reaction mixture can be incubated in a vessel of any useful configuration. In an exemplary embodiment, the vessel is sealed while the reaction mixture is incubated, e.g., a sealed tube.

The following examples illustrate embodiments of the invention and are not intended to limit the scope of the compositions of the invention or the methods in which they find use.

EXAMPLES

Example 1

General Experimental Details

All manipulations were conducted under an inert atmosphere with a nitrogen-filled glovebox unless otherwise noted. All reactions were conducted in oven-dried 4-mL or 20-mL vials fitted with a Teflon-lined screw cap under an atmosphere of nitrogen unless otherwise noted.

Cesium fluoride was purchased from Sigma-Aldrich and dried at 140° C. under vacuum (100 mtorr) for 12 hours prior to use. Trimethyl(trifluoromethyl) silane (TMSCF$_3$, Ruppert's reagent) was purchased from Matrix Scientific. N-Methylpyrrolidone (NMP), 99.5%, Extra Dry over Molecular Sieves, was purchased from Acros and used without further purification. Unless otherwise noted, all other reagents were purchased from commercial suppliers and used as received. Trimethyl(difluoromethyl)silane, 2-((4-iodobenzyl)oxy)tetrahydro-2H-pyran (11) and Z-1-iodo-1-octene (4a) were prepared according to literature procedures. (Tyutyunov, A. A.; Boyko, V. E.; Igoumnov, S. M. *Fluorine Notes* 2011, 74, 1; Mansfeld, U.; Hager, M. D.; Hoogenboom, R.; Ott, C.; Winter, A.; Schubert, U. S. *Chem. Commun.* 2009, 3386; Brown, H. C.; Subrahmanyam, C.; Hamaoka, T.; Ravindran, N.; Bowman, D. H.; Misumi, S.; Unni, M. K.; Somayaji, V.; Bhat, N. G. *J. Org. Chem.* 1989, 54, 6068).

Organic solutions were concentrated by rotary evaporation. Flash column chromatography was performed on Silicylce Siala-P silica gel or on a Teledyne Isco CombiFlash Rf automated chromatography system with 12 g RediSep Rf Gold normal-phase silica columns. The products were visualized by UV light and stained with potassium permanganate (KMnO$_4$).

NMR spectra were acquired on 400 MHz, 500 MHz, or 600 MHz Bruker instruments at the University of California. NMR spectra were processed with MestReNova 5.0 (Mestrelab Research SL). Chemical shifts are reported in ppm and referenced to residual solvent peaks (CHCl$_3$ in CDCl$_3$: 7.26 ppm for $^1$H and 77.0 ppm for $^{13}$C) or to an external standard (1% CFCl$_3$ in CDCl$_3$: 0 ppm for $^{19}$F). Coupling constants are reported in hertz.

All GC-MS analyses were conducted with an Agilent 6890N GC equipped with an HP-5 column (25 m×0.20 mm ID×0.33 μm film) and an Agilent 5973 Mass Selective Detector. The temperature for each run was held at 50° C. for 2 min, ramped from 50° C. to 300° C. at 40° C./min, and held at 300° C. for 5 min.

1.1 Preparation of 1-(1,1-diethoxyethyl)-4-iodobenzene (1h)

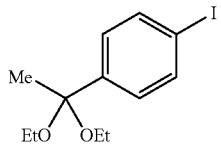 [SMILES: CCOC(C)(OCC)c1ccc(I)cc1]

To a 3 mL vial was added 4'-iodoacetophenone (492 mg, 2.0 mmol), tetrabutylammonium tribromide (14 mg, 0.03 mmol) and 2 mL of ethanol. Triethylorthoformate (730 µL, 4.4 mmol) was added and the resulting solution was stirred at room temperature for 10 hours. The reaction was poured into 5 mL of saturated NaHCO$_3$ and extracted with ethyl acetate. The organic layer was dried with Na$_2$SO$_4$ and concentrated to an orange oil (530 mg, 1.7 mmol, 85% yield). $^1$H NMR (500 MHz, CDCl$_3$) δ 7.68 (d, J=8.4 Hz, 2H), 7.29 (d, J=8.5 Hz, 2H), 3.48 (dq, J=9.3, 7.1 Hz, 2H), 3.40-3.29 (m, 2H), 1.53 (s, 3H), 1.22 (t, J=7.1 Hz, 6H). $^{13}$C NMR (126 MHz, CDCl$_3$) δ 143.68 (s), 137.07 (s), 128.27 (s), 100.88 (s), 93.18 (s), 56.69 (s), 26.92 (s), 15.31 (s).

1.2 Preparation of N-(4-iodophenyl)-N-methylpivalamide (1j)

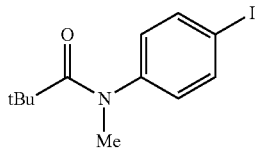 [SMILES: CN(C(=O)C(C)(C)C)c1ccc(I)cc1]

4-iodoaniline (2.19 g, 10 mmol), 4-dimethylaminopyridine (DMAP, 12 mg, 0.1 mmol), and pyridine (1.6 mL, 20 mmol) were dissolved in 20 mL of CH$_2$Cl$_2$ and cooled to 0° C. Pivaloyl chloride (1.35 mL, 11 mmol) was added dropwise, and the resulting solution was allowed to warm to room temperature and stirred a total of 3 h. The solution was poured into a separatory funnel and washed with 1×20 mL of 1 M HCl and 1×20 mL of saturated NaHCO$_3$. The organic layer was dried with MgSO$_4$ and concentrated to a white solid (2.90 g, 9.6 mmol).

500 mg of the white solid, N-(4-iodophenyl)pivalamide (1.65 mmol), was dissolved in 2 mL of anhydrous THF and added dropwise to a suspension of 60% NaH (79 mg, 2.0 mmol) in 1 mL of anhydrous THF. The resulting solution was stirred at room temperature for 30 minutes, and methyl iodide (160 µL, 2.5 mmol) was added dropwise. After stirring for 3 h, water was added, and the product was extracted with ether. Drying with MgSO$_4$ and removal of the solvent gave 1j as a white solid (480 mg, 1.5 mmol, 92% yield). $^1$H NMR (400 MHz, CDCl$_3$) δ 7.74-7.70 (m, 2H), 6.99-6.95 (m, 2H), 3.18 (s, 3H), 1.05 (s, 6H). $^{13}$C NMR (126 MHz, CDCl$_3$) δ 177.93 (s), 145.12 (s), 138.49 (s), 130.70 (s), 92.73 (s), 41.22 (s), 40.80 (s), 29.45 (s).

1.3 Preparation of N-ethyl-N-(4-iodobenzyl)ethanamine (1k)

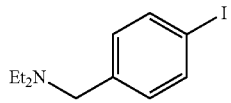

4-iodobenzylbromide (891 mg, 3.0 mmol) was dissolved in 3 mL of CH$_2$Cl$_2$ and diethylamine (930 µL, 9.0 mmol) was added at once. After 20 min at room temperature, the reaction was complete, as judged by TLC analysis. The solution was poured into a separatory funnel containing ethyl acetate and washed with 2×10 mL of 3 M KOH and 1×10 mL of brine. The organic layer was dried over sodium sulfate and concentrated to give 1k as a light yellow oil (830 mg, 2.9 mmol, 96% yield). $^1$H NMR (500 MHz, CDCl$_3$) δ 7.62 (d, J=8.2 Hz, 2H), 7.09 (d, J=8.2 Hz, 2H), 3.49 (s, 2H), 2.49 (q, J=7.1 Hz, 4H), 1.02 (t, J=7.1 Hz, 6H). $^{13}$C NMR (126 MHz, CDCl$_3$) δ 139.93 (s), 137.14 (s), 130.80 (s), 91.80 (s), 57.00 (s), 46.73 (s), 11.75 (s).

1.4 Preparation of 1-bromo-4-((4-iodophenoxy)methyl)benzene (1m)

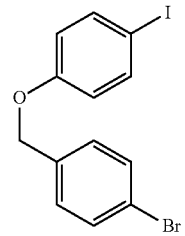 [SMILES: Brc1ccc(COc2ccc(I)cc2)cc1]

Sodium hydride (60% wt/wt in mineral oil, 132 mg, 3.3 mmol) was suspended in 2 mL of anhydrous THF. 4-Iodophenol (660 mg, 3.0 mmol) in 2 mL of THF was added dropwise to the NaH suspension and stirred at room temperature for 5 min. 4'-Bromo-benzylbromide in 2 mL of THF was added dropwise and stirred at 80° C. for 8 h. The solution was washed with water and extracted with ether. The organic layer was washed with 1×10 mL of brine, dried with magnesium sulfate, and concentrated and purified by silica gel chromatography eluting with hexanes (R$_f$=0.15). White solid (1.01 g, 2.6 mmol, 87% yield). $^1$H NMR (500 MHz, CDCl$_3$) δ 7.58-7.54 (m, 2H), 7.53-7.49 (m, 2H), 7.28 (d, J=8.5 Hz, 2H), 6.75-6.69 (m, 2H), 4.98 (s, 2H). $^{13}$C NMR (126 MHz, CDCl$_3$) δ 158.35 (s), 138.31 (s), 135.54 (s), 131.77 (s), 128.99 (s), 122.03 (s), 117.26 (s), 83.31 (s), 69.32 (s).

1.5 Preparation of 4-iodobenzyl pivalate (1n)

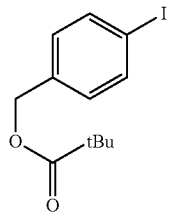 [SMILES: CC(C)(C)C(=O)OCc1ccc(I)cc1]

Sodium hydride (60% wt/wt in mineral oil, 132 mg, 3.3 mmol) was suspended in 3 mL of anhydrous THF. 4'-Iodobenzylalcohol in 2 mL of THF was added dropwise to the NaH suspension and stirred at room temperature for 10 min. Pivaloyl chloride (406 µL, 3.3 mmol) was added dropwise, and the resulting solution was stirred at room temperature for 2 h. The solution was poured into water and extracted with ether. The organic layer was washed with 1×10 mL of saturated NaHCO$_3$ and 1×10 mL of brine, dried with magnesium sulfate, and concentrated to give in as a light yellow oil (905 mg, 2.8 mmol, 95% yield). $^1$H NMR (500 MHz, CDCl$_3$) δ 7.68 (d, J=8.2 Hz, 2H), 7.08 (d, J=8.2 Hz, 2H), 5.04 (s, 2H), 1.22 (s, 9H). $^{13}$C NMR (126 MHz, CDCl$_3$) δ 178.17 (s), 137.59 (s), 136.09 (s), 129.59 (s), 93.57 (s), 65.30 (s), 38.75 (s), 27.13 (s).

1.6 Preparation of (E)-1-(tert-butyl)-4-(2-iodovinyl)benzene (3a)

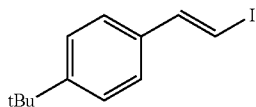 [SMILES: CC(C)(C)c1ccc(/C=C/I)cc1]

To 4-(tert-butyl)-phenylacetylene (1.27 g, 8.0 mmol) in a small vial was slowly added catecholborane (853 µL, 8.0 mmol). The resulting mixture was heated at 70° C. for 2 h and allowed to cool to room temperature, forming an orange solid. The orange solid was dissolved in 20 mL of THF and 8 mL of 3 M NaOH was added slowly and stirred at room temperature for 10 min. A solution of I$_2$ (4.06 g, 16 mmol) in 80 mL of THF was added by an addition funnel over 2 h. The dark reaction mixture was filtered thru Celite, diluted with ethyl acetate and washed 2×20 mL with saturated sodium thiosulfate and 1×10 mL brine. The organic layer was dried with magnesium sulfate and purified by silica gel chromatography eluting with hexanes (R$_f$=0.5) to give a light yellow oil that solidified upon standing (1.43 g, 5.0 mmol, 62% yield). $^1$H NMR (400 MHz, CDCl$_3$) δ 7.40 (d, J=14.9 Hz, 1H), 7.34 (d, J=8.1 Hz, 2H), 7.23 (d, J=8.0 Hz, 2H), 6.76 (d, J=14.9 Hz, 1H), 1.31 (s, 9H). $^{13}$C NMR (126 MHz, CDCl$_3$) δ 151.54 (s), 144.71 (s), 134.99 (s), 125.70 (s), 125.61 (s), 75.55 (s), 34.67 (s), 31.17 (s).

Example 2

General Procedure for the Difluoromethylation of Aryl and Vinyl Iodides

In a nitrogen-filled glove box, aryl or vinyl iodide (0.5 mmol, 1 equiv), copper iodide (0.5 mmol, 1 eq), and cesium fluoride (1.5 mmol, 1 equiv) were combined in a 20 mL vial. To this vial was added 2.5 mL of anhydrous NMP, followed by trimethyl(difluoromethyl)silane (2.5 mmol, 5 equiv). The reaction mixture was heated in a sealed vessel at 120° C. for 24 h. Note: the pressure increases during the reaction due to the formation of volatile fluorotrimethylsilane (Me$_3$SiF) as a stoichiometric product. The dark red solution was then cooled to room temperature, and diluted with 15 mL of Et$_2$O. The mixture was filtered over Celite, washed with an additional 20 mL of Et$_2$O, and transferred to a reparatory funnel. The mixture was washed with 5×20 mL of H$_2$O and 1×20 mL of brine, dried with MgSO$_4$, filtered, and concentrated under vacuum. The crude product was purified by column chromatography on silica gel with pentane or pentane/Et$_2$O mixtures as the eluent.

2.1 1-butyl-4-(difluoromethyl)benzene (2a)

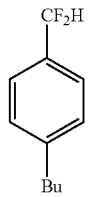

The reaction was performed according to the general procedure for difluoromethylation on a 0.5 mmol scale (89 µL 1a). The crude mixture was purified by silica gel chromatography (12 g of silica, 100:0→90:10 pentane:Et$_2$O) to give 2a (83 mg, 90% yield). $^1$H NMR (400 MHz, CDCl$_3$) δ 7.42 (d, J=7.7 Hz, 2H), 7.27 (d, J=7.2 Hz, 2H), 6.63 (t, J=56.6 Hz, 1H), 1.67-1.56 (m, 2H), 1.37 (dt, J=14.9, 7.3 Hz, 2H), 0.94 (t, J=7.3 Hz, 3H). $^{13}$C NMR (151 MHz, CDCl$_3$) δ 145.82 (t, J=1.9 Hz), 131.77 (t, J=22.4 Hz), 128.68 (s), 125.47 (t, J=6.0 Hz), 114.95 (t, J=238.0 Hz), 35.49 (s), 33.42 (s), 22.28 (s), 13.88 (s). $^{19}$F NMR (376 MHz, CDCl$_3$) δ −110.06 (d, J=56.6 Hz).

2.2 1-(benzyloxy)-4-(difluoromethyl)benzene (2b)

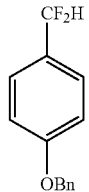

The reaction was performed according to the general procedure for difluoromethylation on a 0.5 mmol scale (155 mg 1b). The crude mixture was purified by silica gel chromatography (12 g of silica, 100:0→90:10 pentane:Et$_2$O) to give 2b (102 mg, 87% yield). $^1$H NMR (400 MHz, CDCl$_3$) δ 7.48-7.31 (m, 7H), 7.03 (d, J=8.5 Hz, 2H), 6.60 (t, J=56.7 Hz, 1H), 5.10 (s, 2H). $^{13}$C NMR (151 MHz, CDCl$_3$) δ 160.51 (t, J=1.6 Hz), 136.46 (s), 128.66 (s), 128.14 (s), 127.43 (s), 127.13 (t, J=5.9 Hz), 127.01 (s), 114.92 (s), 114.83 (t, J=237.5 Hz), 70.09 (s). $^{19}$F NMR (376 MHz, CDCl$_3$) δ −108.77 (d, J=57.0 Hz).

2.3 4-(difluoromethyl)-1,1'-biphenyl (2c)

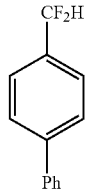

The reaction was performed according to the general procedure for difluoromethylation on a 0.5 mmol scale (140 mg 1c). The crude mixture was purified by silica gel chromatography (12 g of silica, 100:0→90:10 pentane:

Et$_2$O) to give 2c (90 mg, 88% yield). $^1$H NMR (400 MHz, CDCl$_3$) δ 7.68 (d, J=8.0 Hz, 2H), 7.60 (t, J=7.2 Hz, 4H), 7.47 (t, J=7.5 Hz, 2H), 7.39 (t, J=6.9 Hz, 1H), 6.70 (t, J=56.5 Hz, 1H). $^{13}$C NMR (151 MHz, CDCl$_3$) δ 143.70 (t, J=2.0 Hz), 140.18 (s), 133.20 (t, J=22.2 Hz), 128.90 (s), 127.89 (s), 127.42 (s), 127.24 (s), 126.01 (t, J=6.0 Hz), 114.73 (t, J=238.5 Hz). $^{19}$F NMR (376 MHz, C$_6$D$_6$) δ −111.35 (d, J=57.0 Hz).

2.4 1-(difluoromethyl)-3-methoxybenzene (2d)

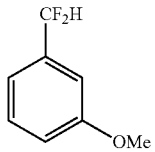

The reaction was performed according to the general procedure for difluoromethylation on a 0.5 mmol scale (59.5 μL 1d). The crude mixture was purified by silica gel chromatography (12 g of silica, 100:0→90:10 pentane:Et$_2$O) to give 2d (64 mg, 81% yield). $^1$H NMR (600 MHz, CDCl$_3$) δ 7.36 (t, J=7.9 Hz, 1H), 7.08 (d, J=7.5 Hz, 1H), 7.04 (s, 1H), 7.01 (d, J=8.3 Hz, 1H), 6.61 (t, J=56.5 Hz, 1H), 3.84 (s, 3H). $^{13}$C NMR (151 MHz, CDCl$_3$) δ 159.82 (s), 135.75 (t, J=22.3 Hz), 129.86 (s), 117.82 (t, J=6.3 Hz), 116.59 (t, J=1.8 Hz), 114.55 (t, J=239.0 Hz), 110.66 (t, J=6.1 Hz), 55.36 (s). $^{19}$F NMR (376 MHz, CDCl$_3$) δ −111.12 (d, J=56.5 Hz).

2.5 1-(difluoromethyl)-3,5-dimethylbenzene (2e)

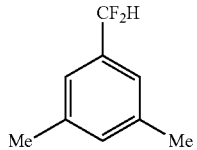 [SMILES: Cc1cc(C)cc(C(F)F)c1]

The reaction was performed according to the general procedure for difluoromethylation on a 0.5 mmol scale (72.2 μL 1e). The crude mixture was purified by silica gel chromatography (12 g of silica, 100:0→90:10 pentane:Et$_2$O) to give 2e (58 mg, 74% yield). $^1$H NMR (600 MHz, CDCl$_3$) δ 7.12 (s, 2H), 7.10 (s, 1H), 6.57 (t, J=56.6 Hz, 1H), 2.36 (s, 6H). $^{13}$C NMR (151 MHz, CDCl$_3$) δ 138.44 (s), 134.30 (t, J=21.7 Hz), 132.27 (t, J=1.9 Hz), 123.20 (t, J=6.0 Hz), 114.99 (t, J=238.4 Hz), 21.21 (s). $^{19}$F NMR (376 MHz, CDCl$_3$) δ −110.61 (d, J=56.7 Hz).

2.6 2-(difluoromethyl)-1,3-dimethylbenzene (2f)

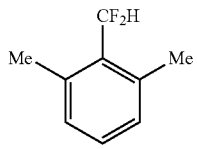

The reaction was performed according to the general procedure for difluoromethylation on a 0.5 mmol scale (116 mg 1f). The crude mixture was purified by silica gel chromatography (12 g of silica, 100:0→90:10 pentane:Et$_2$O) to give 2f (75 mg, 48% yield). $^1$H NMR (600 MHz, CDCl$_3$) δ 7.22 (t, J=7.6 Hz, 1H), 7.05 (d, J=7.6 Hz, 2H), 6.99 (t, J=54.3 Hz, 1H), 2.48 (s, 6H). $^{13}$C NMR (151 MHz, CDCl$_3$) δ 137.05 (t, J=4.0 Hz), 130.31 (t, J=1.5 Hz), 130.00 (t, J=20.3 Hz), 129.18 (s), 114.48 (t, J=236.2 Hz), 19.45 (t, J=1.4 Hz). $^{19}$F NMR (376 MHz, CDCl$_3$) δ −113.15 (d, J=54.3 Hz).

2.7 1-(tert-butyl)-4-(difluoromethyl)benzene (2g)

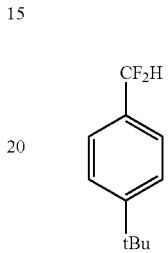

The reaction was performed according to the general procedure for difluoromethylation on a 0.5 mmol scale (130 mg 1g). The crude mixture was purified by silica gel chromatography (12 g of silica, 100:0→90:10 pentane: Et$_2$O) to give 2g (113 mg, 61% yield). A small amount (<10%) of unreacted 1g was unable to be separated from the product. $^1$H NMR (500 MHz, CDCl$_3$) δ 7.47 (q, J=8.5 Hz, 4H), 6.63 (t, J=56.6 Hz, 1H), 1.34 (s, 9H). $^{13}$C NMR (151 MHz, CDCl$_3$) δ 154.00 (t, J=2.0 Hz), 131.54 (t, J=22.4 Hz), 125.61 (s), 125.30 (t, J=6.0 Hz), 114.90 (t, J=238.0 Hz), 34.85 (s), 31.21 (s). $^{19}$F NMR (376 MHz, CDCl$_3$) δ −110.24 (d, J=56.6 Hz).

2.8 1-(1,1-diethoxyethyl)-4-(difluoromethyl)benzene (2h)

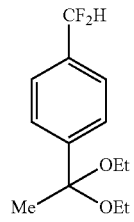

The reaction was performed according to the general procedure for difluoromethylation on a 0.5 mmol scale (160 mg 1h). The crude mixture was purified by silica gel chromatography (12 g of silica, 100:0→90:10 pentane: Et$_2$O) to give 2h (101 mg, 82% yield). $^1$H NMR (600 MHz, CDCl$_3$) δ 7.62 (d, J=7.8 Hz, 2H), 7.48 (d, J=7.8 Hz, 2H), 6.65 (t, J=56.4 Hz, 1H), 3.53-3.44 (m, 2H), 3.39-3.31 (m, 2H), 1.22 (t, J=7.0 Hz, 6H). $^{13}$C NMR (151 MHz, CDCl$_3$) δ 146.74 (s), 133.43 (t, J=22.4 Hz), 126.58 (s), 125.27 (t, J=5.9 Hz), 114.76 (t, J=238.3 Hz), 100.94 (s), 56.77 (s), 27.04 (s), 15.29 (s). $^{19}$F NMR (376 MHz, CDCl$_3$) δ −110.72 (d, J=56.5 Hz).

2.9 1-(difluoromethyl)-2-methoxybenzene (2i)

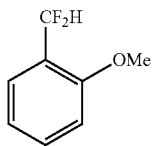

The reaction was performed according to the general procedure for difluoromethylation on a 0.5 mmol scale (117 mg 1i). The crude mixture was purified by silica gel chromatography (12 g of silica, 100:0→90:10 pentane:Et$_2$O) to give 2i (24 mg, 30% yield). $^1$H NMR (600 MHz, CDCl$_3$) δ 7.57 (d, J=7.5 Hz, 1H), 7.43 (t, J=7.8 Hz, 1H), 7.04 (d, J=8.3 Hz, 1H), 6.95 (t, J=47.5 Hz, 1H), 6.94 (d, J=8.4 Hz, 1H), 3.87 (s, 3H). $^{13}$C NMR (151 MHz, CDCl$_3$) δ 157.27 (t, J=6.0 Hz), 131.94 (t, J=1.9 Hz), 126.22 (t, J=5.8 Hz), 122.71 (t, J=22.0 Hz), 120.59 (s), 113.13 (s), 110.82 (t, J=117.7 Hz), 55.59 (s). $^{19}$F NMR (376 MHz, CDCl$_3$) δ −115.84 (d, J=55.7 Hz).

2.10 N-(4-(difluoromethyl)phenyl)-N-methylpivalamide (2j)

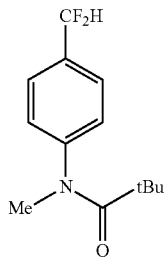

The reaction was performed according to the general procedure for difluoromethylation on a 0.5 mmol scale (159 mg 1j). The crude mixture was purified by silica gel chromatography (6:1 Hexanes:Ethyl Acetate, R$_f$=0.13) to give 2j (63 mg, 52% yield). $^1$H NMR (500 MHz, CDCl$_3$) δ 7.54 (d, J=8.1 Hz, 2H), 7.31 (d, J=8.1 Hz, 2H), 6.67 (t, J=56.3 Hz, 1H), 3.21 (s, 3H), 1.04 (s, 9H). $^{13}$C NMR (126 MHz, CDCl$_3$) δ 178.01 (s), 147.52 (t, J=2.0 Hz), 133.74 (t, J=22.7 Hz), 129.05 (s), 126.64 (t, J=5.9 Hz), 114.04 (t, J=239.2 Hz), 41.22 (s), 40.82 (s), 29.39 (s). $^{19}$F NMR (376 MHz, CDCl$_3$) δ −111.24 (d, J=56.3 Hz).

2.11 N-(4-(difluoromethyl)benzyl)-N-ethylethanamine (2k)

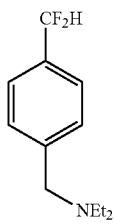

The reaction was performed according to the general procedure for difluoromethylation on a 0.5 mmol scale (145 mg 1k). The crude mixture was purified by silica gel chromatography (3:1 Hexanes:Ethyl Acetate, R$_f$=0.2) to give 2k (63 mg, 59% yield). A small amount (<5%) of unreacted 1k was unable to be separated from the product. $^1$H NMR (500 MHz, CDCl$_3$) δ 7.49-7.40 (m, 4H), 6.63 (t, J=56.6 Hz, 1H), 3.59 (s, 2H), 2.52 (q, J=7.1 Hz, 4H), 1.04 (t, J=7.1 Hz, 6H). $^{13}$C NMR (126 MHz, CDCl$_3$) δ 143.20 (s), 132.74 (t, J=22.3 Hz), 128.97 (s), 125.37 (t, J=6.0 Hz), 114.86 (t, J=238.1 Hz), 57.23 (s), 46.79 (s), 11.75 (s). $^{19}$F NMR (376 MHz, CDCl$_3$) δ −111.17 (d, J=56.6 Hz).

2.12 2-((4-(difluoromethyl)benzyl)oxy)tetrahydro-2H-pyran (2l)

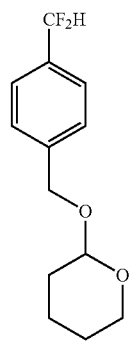

The reaction was performed according to the general procedure for difluoromethylation on a 0.5 mmol scale (159 mg 1l). The crude mixture was purified by silica gel chromatography (6:1 Hexanes:Ethyl Acetate, R=0.49) to give 2l (85 mg, 70% yield). $^1$H NMR (500 MHz, CDCl$_3$) δ 7.47 (dd, J=18.5, 8.2 Hz, 4H), 6.64 (t, J=56.5 Hz, 1H), 4.83 (d, J=12.5 Hz, 1H), 4.71 (t, J=3.5 Hz, 1H), 4.55 (d, J=12.5 Hz, 1H), 3.91 (ddd, J=11.4, 8.6, 2.9 Hz, 1H), 3.58-3.53 (m, 1H), 1.92-1.83 (m, 1H), 1.80-1.72 (m, 1H), 1.71-1.51 (m, 4H). $^{13}$C NMR (126 MHz, CDCl$_3$) δ 141.23 (t, J=1.9 Hz), 133.49 (t, J=22.4 Hz), 127.78 (s), 125.61 (t, J=6.0 Hz), 114.68 (t, J=238.4 Hz), 97.90 (s), 68.19 (s), 62.16 (s), 30.50 (s), 25.41 (s), 19.29 (s). $^{19}$F NMR (376 MHz, CDCl$_3$) δ −111.33 (d, J=56.6 Hz).

2.13 1-bromo-4-((4-(difluoromethyl)phenoxy)methyl)benzene (2m)

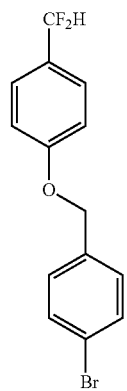 [SMILES: FC(F)c1ccc(OCc2ccc(Br)cc2)cc1]

The reaction was performed according to the general procedure for difluoromethylation on a 0.5 mmol scale (195 mg 1m). The crude mixture was purified by silica gel chromatography (12 g of silica, 100:0→90:10 pentane:Et$_2$O) to give 2m (121 mg, 77% yield). A small amount (<5%) of unreacted 1m was unable to be separated from the product. $^1$H NMR (400 MHz, CDCl$_3$) δ 7.52 (d, J=8.1 Hz, 2H), 7.44 (d, J=8.2 Hz, 2H), 7.31 (d, J=8.2 Hz, 2H), 7.00 (d, J=8.4 Hz, 2H), 6.60 (t, J=56.7 Hz, 1H), 5.05 (s, 2H). $^{13}$C NMR (126 MHz, CDCl$_3$) δ 160.16 (t, J=1.8 Hz), 135.43 (s), 131.77 (s), 129.51 (s), 129.01 (s), 127.17 (t, J=5.9 Hz), 122.05 (s), 114.84 (s), 114.74 (t, J=237.6 Hz), 69.26 (s). $^{19}$F NMR (376 MHz, CDCl$_3$) δ −108.86 (d, J=56.7 Hz).

2.14 4-(difluoromethyl)benzyl pivalate (2n)

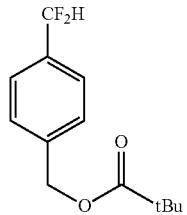 [SMILES: CC(C)(C)C(=O)OCc1ccc(C(F)F)cc1]

The reaction was performed according to the general procedure for difluoromethylation on a 0.5 mmol scale (159 mg 1n). The crude mixture was purified by silica gel chromatography (12 g of silica, 100:0→90:10 pentane:Et$_2$O) to give 2n (63 mg, 52% yield). A small amount (<5%) of unreacted 1n was unable to be separated from the product. $^1$H NMR (600 MHz, CDCl$_3$) δ 7.51 (d, J=7.7 Hz, 1H), 7.42 (d, J=7.7 Hz, 1H), 6.65 (t, J=56.5 Hz, 1H), 5.14 (s, 1H), 1.24 (s, 4H). $^{13}$C NMR (151 MHz, CDCl$_3$) δ 178.19 (s), 139.26 (t, J=1.8 Hz), 134.04 (t, J=22.5 Hz), 127.79 (s), 125.78 (t, J=6.0 Hz), 114.50 (t, J=238.8 Hz), 65.35 (s), 38.81 (s), 27.16 (s). $^{19}$F NMR (376 MHz, CDCl$_3$) δ −111.03 (d, J=56.7 Hz).

2.15 (E)-1-(tert-butyl)-4-(3,3-difluoroprop-1-en-1-yl)benzene (4a)

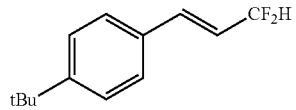 [SMILES: CC(C)(C)c1ccc(/C=C/C(F)F)cc1]

The reaction was performed according to the general procedure for difluoromethylation on a 0.5 mmol scale (143 mg 3a). The crude mixture was purified by silica gel chromatography (Hexanes, R$_f$=0.27) to give 4a (84 mg, 80% yield). $^1$H NMR (500 MHz, CDCl$_3$) δ 7.44-7.36 (m, 4H), 6.90-6.82 (m, 1H), 6.38-6.12 (m, 2H), 1.34 (s, 9H). $^{13}$C NMR (126 MHz, CDCl$_3$) δ 152.75 (s), 136.93 (t, J=12.2 Hz), 131.63 (s), 127.01 (s), 125.74 (s), 120.12 (t, J=23.9 Hz), 115.61 (t, J=233.3 Hz), 34.74 (s), 31.18 (s). $^{19}$F NMR (376 MHz, CDCl$_3$) δ −109.42−−109.69 (m).

2.16 (E)-1,1-difluoronon-2-ene (4b)

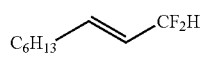

The reaction was performed according to the general procedure for difluoromethylation on a 0.5 mmol scale (119 mg 3b). The crude mixture was purified by silica gel chromatography (12 g of silica, 100:0→90:10 pentane:Et$_2$O) to give 4b (74 mg, 91% yield). $^1$H NMR (600 MHz, CDCl$_3$) δ 6.07 (ddd, J=9.8, 7.0, 3.3 Hz, 1H), 6.02 (td, J=56.2, 6.0 Hz, 1H), 5.63 (dt, J=15.4, 7.6 Hz, 1H), 2.17-2.08 (m, 2H), 1.45-1.38 (m, 2H), 1.34-1.25 (m, 6H), 0.89 (t, J=6.6 Hz, 3H). $^{13}$C NMR (151 MHz, CDCl$_3$) δ 140.26 (t, J=11.9 Hz), 123.17 (t, J=23.8 Hz), 115.57 (t, J=232.8 Hz), 31.79 (s), 31.59 (s), 28.72 (s), 28.20 (t, J=1.9 Hz), 22.54 (s), 14.02 (s). $^{19}$F NMR (376 MHz CDCl$_3$) δ −110.86−−111.08 (m).

2.17 (Z)-1,1-difluoronon-2-ene (4c)

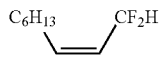

The reaction was performed according to the general procedure for difluoromethylation on a 0.5 mmol scale (119 mg 3b). The crude mixture was purified by silica gel chromatography (12 g of silica, 100:0→90:10 pentane:Et$_2$O) to give 4b (34 mg, 42% yield). $^1$H NMR (400 MHz, CDCl$_3$) δ 6.39 (td, J=56.0, 6.9 Hz, 1H), 5.93-5.83 (m, 1H), 5.65-5.51 (m, 1H), 2.17 (q, J=7.5 Hz, 2H), 1.45-1.36 (m, 2H), 1.36-1.22 (m, 6H), 0.88 (t, J=6.5 Hz, 3H). $^{13}$C NMR (126 MHz, CDCl$_3$) δ 140.04 (t, J=12.1 Hz), 122.75 (t, J=25.1 Hz), 111.91 (t, J=231.0 Hz), 31.55 (s), 29.07 (t, J=1.7 Hz), 28.69 (s), 27.90 (t, J=1.4 Hz), 22.53 (s), 14.01 (s). $^{19}$F NMR (376 MHz, CDCl$_3$) δ −111.16 (d, J=56.0 Hz).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A reaction mixture for forming a difluoromethyl aryl compound or a difluoromethyl vinyl compound, said reaction mixture comprising:
   (i) a member selected from an X-substituted precursor of said difluoromethyl aryl compound and an X-substituted precursor of said difluoromethyl vinyl compound, said compound optionally further substituted at one or more positions
   wherein
      X is a leaving group;
   (ii) a Cu source;
   (iii) a fluoride ion source;
   (iv) a silane having the formula:

$R^1R^2R^3SiCF_2H$, wherein
      $R^1$, $R^2$ and $R^3$ are independently selected from substituted or unsubstituted alkyl, substituted or unsubstituted alkoxy and substituted or unsubstituted aryl moieties.

2. The reaction mixture according to claim 1, wherein said precursor is further substituted with a member selected from amine, ether, amide, ester, halide, protected alcohol and a combination thereof.

3. The reaction mixture according to claim 1, further comprising a polar organic solvent.

4. The reaction mixture according claim 1, further comprising N-methylpyrrolidone as a solvent.

5. The reaction mixture according claim 1, wherein said Cu source is a Cu(I) source.

6. The reaction mixture according to claim 1, wherein said Cu source is a member selected from a copper salt and a copper complex.

7. The reaction mixture according to claim 1, wherein said Cu source is a Cu(I) source which is CuI.

8. The reaction mixture according to claim 1, wherein each of $R^1$, $R^2$ and $R^3$ is methyl.

9. The reaction mixture according claim 1, wherein when said aryl compound is further substituted with one or more substituents, the net electronic effect of said one or more substituents on the aryl moiety of said aryl compound is electron neutral or electron donating.

10. The reaction mixture according to claim 1, wherein said precursor, said Cu source, said fluoride ion source and said silane are present in said mixture in a ratio of about 1:1:3:5.

11. The reaction mixture according to claim 1, wherein said precursor of said difluoromethyl aryl compound has an aryl moiety with the formula:

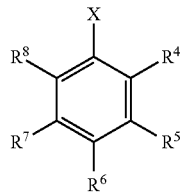

wherein
$R^4$, $R^5$, $R^6$, $R^7$, and $R^8$ are independently members selected from H, substituted or unsubstituted alkyl, substituted or unsubstituted heteroalkyl, substituted or unsubstituted aryl, substituted or unsubstituted heteroaryl, halogen, CN, $CF_3$, acyl, $-SO_2NR^9R^{10}$, $-NR^9R^{10}$, $-OR^9$, $-S(O)_2R^9$, $-C(O)R^9$, $-COOR^9$, $-CONR^9R^{10}$, $-S(O)_2OR^9$, $-OC(O)R^9$, $-C(O)NR^9R^{10}$, $-NR^9C(O)R^{10}$, $-NR^9SO_2R^{10}$ and $-NO_2$, wherein two or more of $R^4$, $R^5$, $R^6$, $R^7$ and $R^8$, together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl wherein
$R^9$ and $R^{10}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and $R^9$ and $R^{10}$, together with the atoms to which they are bonded, are optionally joined to form a 5- to 7-membered ring which is a member selected from substituted or unsubstituted cycloalkyl, substituted or unsubstituted heterocycloalkyl, substituted or unsubstituted aryl and substituted or unsubstituted heteroaryl,
wherein the moieties $R^4$, $R^5$, $R^6$, $R^7$, and $R^8$ are selected such that the net electronic effect of these moieties on the aryl moiety of said precursor is electron neutral or electron donating.

12. The reaction mixture, according claim 1, further comprising a member selected from said difluoromethyl aryl compound or said difluoromethyl vinyl compound.

13. The reaction mixture according to claim 1, wherein said difluoromethyl aryl compound has a formula according to Table 2.

14. The reaction mixture according to claim 1, wherein said precursor of said difluoromethyl vinyl compound has the formula:

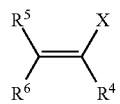

wherein
$R^4$, $R^5$, and $R^6$ are independently members selected from H, substituted or unsubstituted alkyl, substituted or unsubstituted heteroalkyl, substituted or unsubstituted aryl, substituted or unsubstituted heteroaryl, halogen, CN, $CF_3$, acyl, $-SO_2NR^9R^{10}$, $-NR^9R^{10}$, $-OR^9$, $-S(O)_2R^9$, $-C(O)R^9$, $-COOR^9$, $-CONR^9R^{10}$, $-S(O)_2OR^9$, $-OC(O)R^9$, $-C(O)NR^9R^{10}$, $-NR^9C(O)R^{10}$, $-NR^9SO_2R^{10}$ and $-NO_2$, wherein two or more of $R^4$, $R^5$, $R^6$, $R^7$ and $R^8$, together with the atoms to which they are bonded, are optionally joined to form a ring system which is member selected from substituted or unsubstituted cycloalkyl, substituted or unsubstituted heterocycloalkyl, substituted or unsubstituted aryl and substituted or unsubstituted heteroaryl wherein
$R^9$ and $R^{10}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and $R^9$ and $R^{10}$, together with the atoms to which they are bonded, are optionally joined to form a 5- to 7-membered ring.

15. The reaction mixture according to claim 1, wherein said difluoromethyl vinyl compound has a formula according to Table 3.

16. The reaction mixture according to claim 1, wherein X is selected from iodo and bromo.

17. A method for forming a difluoromethyl aryl compound or a difluoromethyl vinyl compound, said method comprising:
(a) forming a reaction mixture according to claim 1; and
(b) incubating said reaction mixture under conditions appropriate to form said difluoromethyl aryl compound or said difluoromethyl vinyl compound by substituting X with a $CF_2H$ moiety.

18. The method according to claim 17, wherein said reaction mixture is incubated at a temperature from about 50° C. to about 180° C.

19. The method according to claim 18, wherein said reaction mixture is incubated at a temperature from about 80° C. to about 140° C.

20. The method according to claim 17, wherein said mixture is incubated in a sealed tube.

21. The method according to claim 17, wherein said mixture is incubated for about 1 hour to about 36 hours.

22. The method according to claim 17, wherein said mixture is incubated for about 6 hours to about 24 hours.

23. The method according to claim 1, wherein said Cu source is selected from CuI and Cu bound to a member selected from substituted or unsubstituted aryl, substituted or unsubstituted heteroaryl, and substituted or unsubstituted secondary or tertiary alkyl moieties.

24. The method according to claim 1, wherein said ligand-bound Cu source is selected from Cu bound to a phenanthroline moiety.

25. A reaction mixture for forming a difluoromethyl aryl compound or a difluoromethyl vinyl compound, said reaction mixture comprising:
(i) a member selected from an X-substituted precursor of said difluoromethyl aryl compound and an X-substituted precursor of said difluoromethyl vinyl compound, said compound optionally further substituted at one or more positions
wherein
X is a leaving group;
(ii) a Cu source;
(iii) a fluoride ion source;
(iv) a silane having the formula:

$R^1R^2R^3SiCF_2H$, wherein
$R^1$, $R^2$ and $R^3$ are independently selected from substituted or unsubstituted alkyl, substituted or unsubstituted alkoxy and substituted or unsubstituted aryl moieties,
said reaction mixture further comprising said difluoromethyl aryl compound or said difluorovinyl compound.

* * * * *

UNITED STATES PATENT AND TRADEMARK OFFICE
CERTIFICATE OF CORRECTION

PATENT NO. : 9,475,756 B2  
APPLICATION NO. : 14/382991  
DATED : October 25, 2016  
INVENTOR(S) : Hartwig et al.

Page 1 of 1

It is certified that error appears in the above-identified patent and that said Letters Patent is hereby corrected as shown below:

In the Specification

Column 1, Line 18 please amend the paragraph below the STATEMENT AS TO RIGHTS TO INVENTIONS MADE UNDER FEDERALLY SPONSORED RESEARCH AND DEVELOPMENT as follows:

This invention was made with Government support under Grant No. GM058108 awarded by the National Institutes of Health. The Government has certain rights in the invention.

Signed and Sealed this
Twenty-fifth Day of April, 2017

Michelle K. Lee
*Director of the United States Patent and Trademark Office*